(12) United States Patent
Kirimura et al.

(10) Patent No.: US 7,393,935 B1
(45) Date of Patent: Jul. 1, 2008

(54) METHOD OF SELECTIVE ARRANGEMENT OF FERRITIN

(75) Inventors: Hiroya Kirimura, Kyoto (JP); Ichiro Yamashita, Nara (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 50 days.

(21) Appl. No.: 11/385,006

(22) Filed: Mar. 21, 2006

Related U.S. Application Data

(63) Continuation of application No. PCT/JP2005/021511, filed on Nov. 24, 2005.

(30) Foreign Application Priority Data

| Dec. 14, 2004 | (JP) | ............................. 2004-361939 |
| Feb. 10, 2005 | (JP) | ............................. 2005-034311 |

(51) Int. Cl.
*C07K 14/00* (2006.01)
*H01L 21/00* (2006.01)
*H01L 21/314* (2006.01)
*H01L 21/471* (2006.01)

(52) U.S. Cl. ........................... 530/400; 438/1; 438/778; 435/7.1

(58) Field of Classification Search ................. 428/328; 530/400; 435/7.1; 438/1, 778
See application file for complete search history.

(56) References Cited

U.S. PATENT DOCUMENTS 6,303,516 B1    10/2001    Morita et al.

2002/0192968 A1    12/2002    Yamashita
2005/0164132 A1    7/2005    Moll et al.

FOREIGN PATENT DOCUMENTS

JP    11-204774    7/1999

OTHER PUBLICATIONS

Yoon, H.C., et al. 2004 Analytical Sciences 20: 1249-1253.*
Grant, A.W., et al. 2004 Nanotechnology 15: 1175-1181.*
Ken-Ichi Sano and Kiyotaka Shiba, "A Hexapeptide Motif that Electrostatically Binds to the Surface of Titanium", J. Am. Chem. Soc. 2003, 125, 14234-14235.
Blawas, A., et al. "Protein Patterning" Biomaterials, Apr. 1998, vol. 19, Issues 7-9, pp. 595-609.
Bernard, A., et al. "Microcontact Printing of Proteins" Advanced Materials, Jul. 2000, vol. 12, Issue 14, pp. 1067-1070.
Lee, K., et al. "Protein Nanoarrays Generated by Dip-Pen Nanolithography" Science, Feb. 2002, vol. 295, No. 5560, pp. 1702-1705.
Zhang, Y., et al. "Imaging As-grown Single-walled carbon nanotubes originated from isolated catalytic nanoparticles" Applied Physics A, 2002, vol. 74, pp. 325-328.

* cited by examiner

*Primary Examiner*—Maryam Monshipouri
*Assistant Examiner*—Marsha M Tsay
(74) *Attorney, Agent, or Firm*—McDermott Will & Emery LLP

(57) ABSTRACT

A method for selectively arranging ferritin in a specified inorganic material part formed on a substrate is provided. The method for arranging ferritin of the present invention is characterized in that ferritin is selectively arranged on a part including titanium or silicon nitride (SiN) in an efficient manner by adding a nonionic surface active agent. Also, selective arrangement capability of ferritin can be markedly improved by modifying the N-terminus of ferritin with a certain peptide.

11 Claims, 16 Drawing Sheets

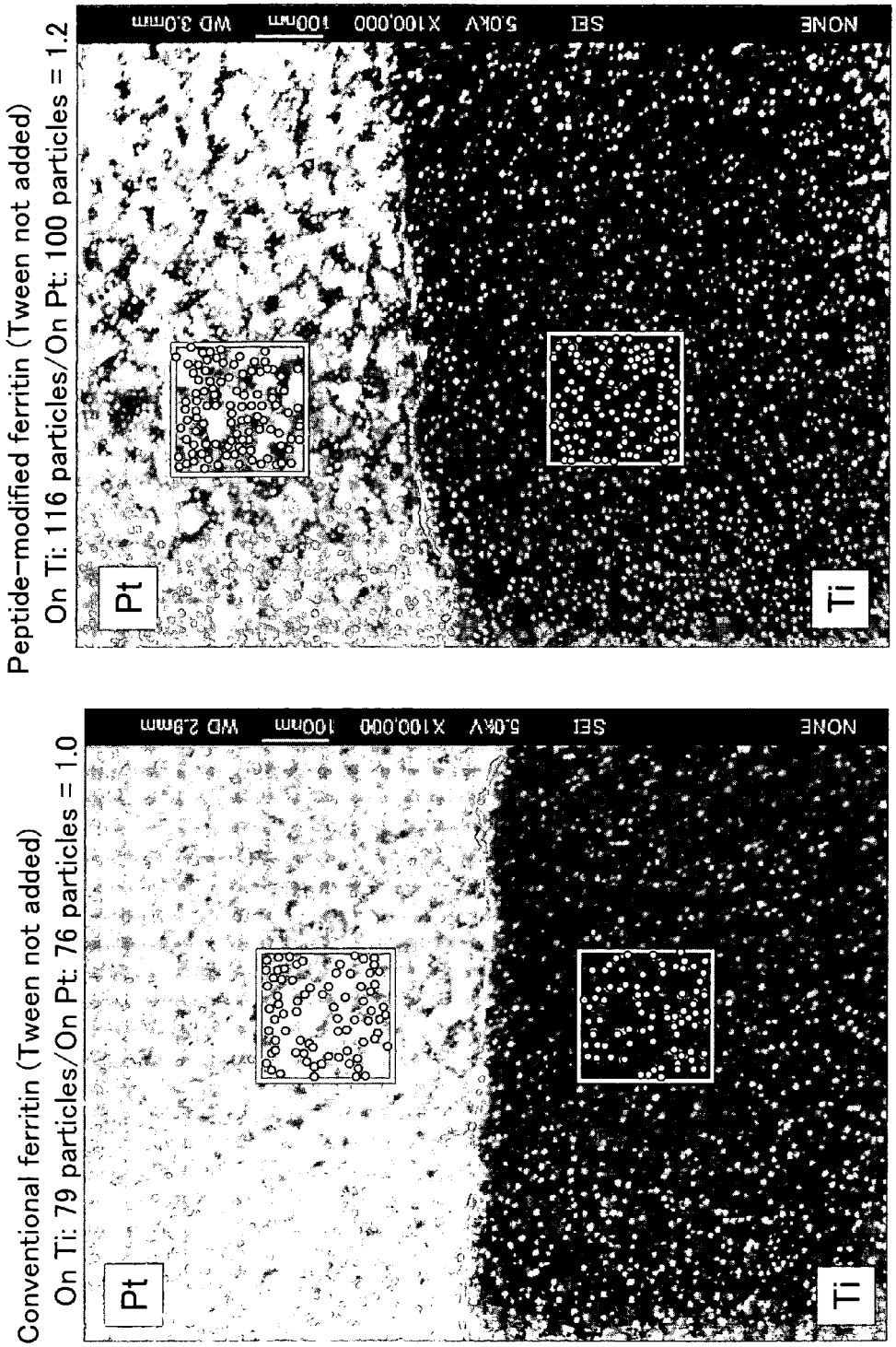

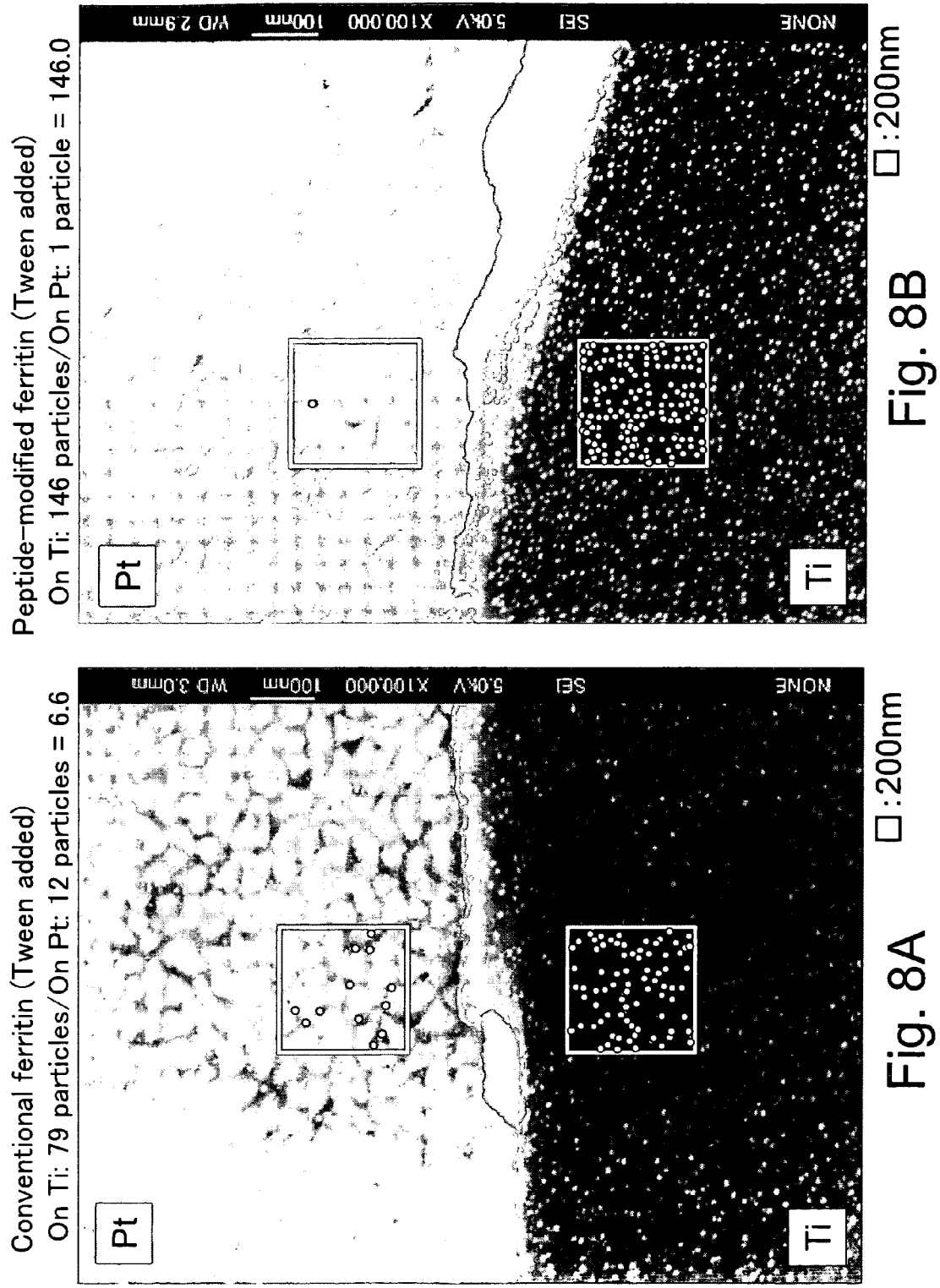

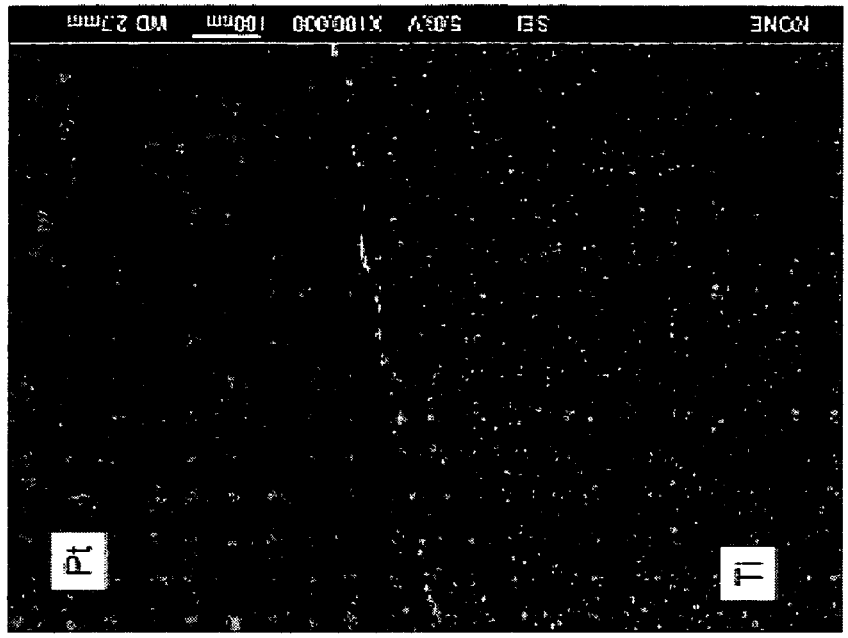
Fig. 9B Tween 80
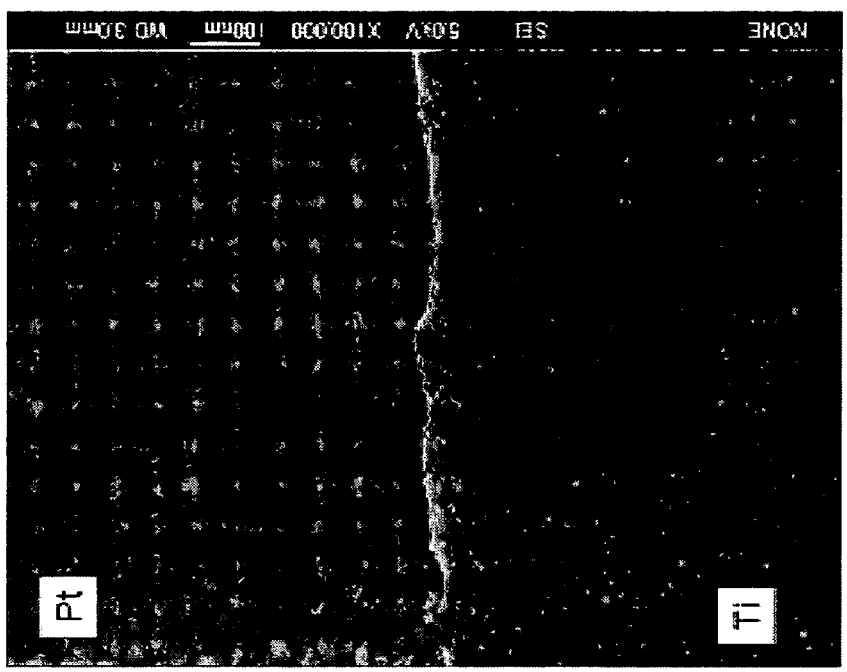
Fig. 9A Tween 20

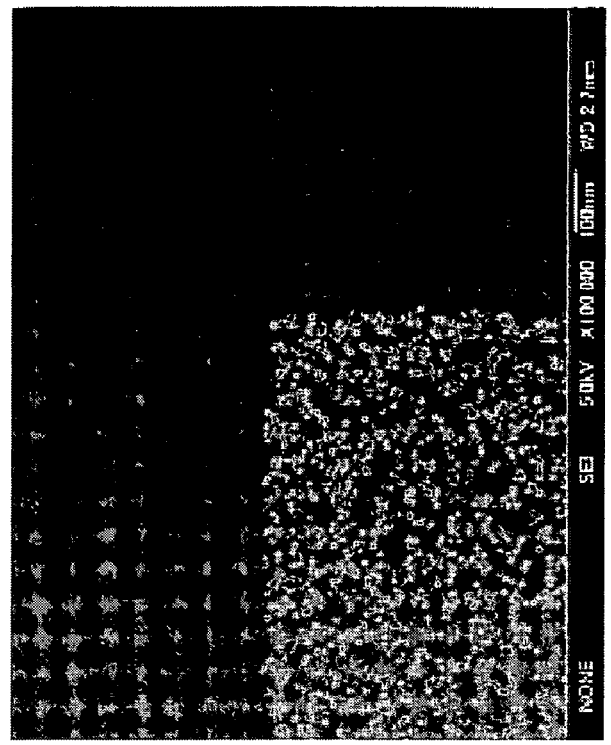
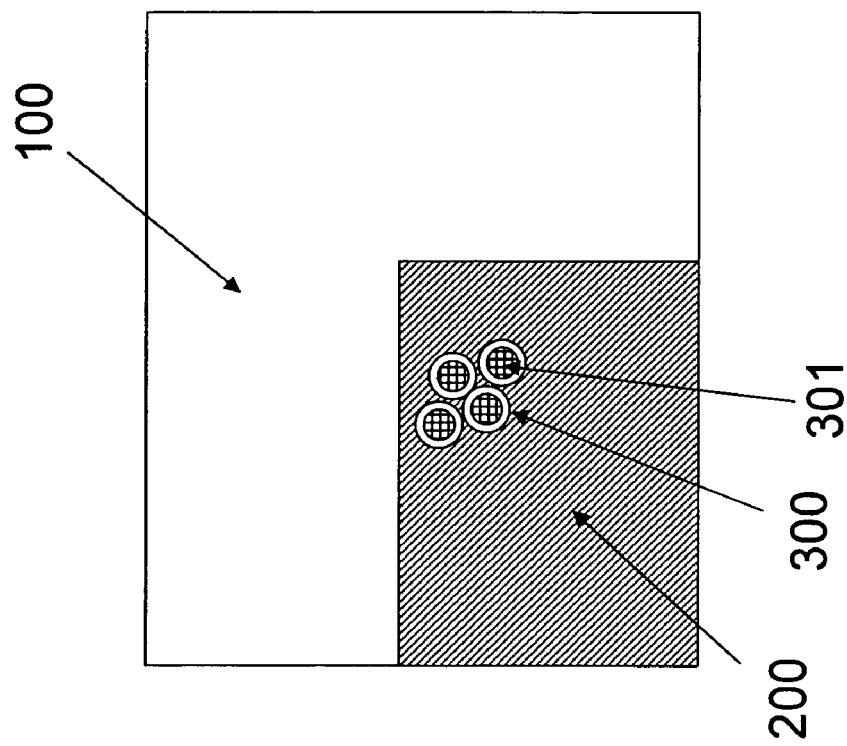
Fig. 10B
Fig. 10A

SiO₂ substrate surface

Ti membrane surface

SiN membrane
surface

SiO₂ substrate
surface

SiN membrane surface

SiO₂ substrate surface

METHOD OF SELECTIVE ARRANGEMENT OF FERRITIN

This is a continuation application under U.S.C 111 (a) of pending prior International application No. PCT/JP2005/021511, filed on Nov. 24, 2005 which in turn claims the benefit of Japanese Application No. 2004-361939 filed on Dec. 14, 2004, and Japanese Application No. 2005-034311 filed on Feb. 10, 2005, the disclosures of which Applications are incorporated by reference herein.

BACKGROUND OF THE INVENTION

1. Field of the Invention

The present invention relates to a method for selectively arranging ferritin.

2. Related Art

Fine particles (inorganic particles) which include a protein and an inorganic substance and which are arranged on a base material have attracted attention in industrial fields of catalysts, sensors, biochips, transistors, semiconductors lasers, magnetic discs, displays and the like. In particular, patterning techniques have been desired in which inorganic particles are selectively arranged in a specified region, or they are regularly arranged in a fine region of nano-size, when the inorganic particles are industrially applied. Furthermore, in recent years, aiming at miniaturization of total analysis systems including biosensors, applications to fine chemical substance analysis systems (Micro Total Analysis System (μTAS)) have also attracted attention. Behind such a situation, advantages such as improvement of biocompatibility, enablement of lowering of the cost by mass productivity and measurement in the place (portable) and the like are involved.

Techniques for selectively arranging proteins or inorganic particles on a solid surface involve extraordinary difficulty because it is very difficult to allow the surface of the protein and the inorganic substance to have a self-recognizing function. Known methods for forming a fine pattern using a protein that is a biomolecule include a method in which photolithography is utilized (see, A. S. Blawas, W. M. Reichert, *Biomaterials*, 19, 595 (1998)), microcontact printing (see, A. Bernard, J. P. Renault, B. Michel, H. R. Bosshard, E. Delamarche, *Adv. Mater.*, 12, 1067), dip-pen nanolithography (see, K. B. Lee, S. J. Park, C. A. Mirkin, J. C. Smith, M. Mrksick, *Science*, 295, 1702 (2002)), and the like. However, in light of mass productivity and costs, techniques for carrying out patterning of fine particles in a nano-size region have been demanded.

Furthermore, a method for regularly arranging nano-size fine particles surrounded by protein molecules is disclosed in Japanese Patent Provisional Publication No. H11-204774. In these methods, procedures of: subjecting the surface of a SAM membrane (self-assembled monomolecular membrane), an LB membrane (monomolecule accumulating membrane) or the like to a processing for selectively arranging the fine particles; executing patterning of the fine particles through further conducting photolithography in combination; forming a region in which the inorganic particles are selectively arranged on the surface of a base material by direct drawing or the like of a pattern on the base material with a nanoprobe such as AFM (Atomic Force Microscope) or the like; and thereafter arranging the inorganic particles.

Hereinafter, a method for arranging inorganic particles using an LB membrane (PBLH membrane) according to the conventional method (Japanese Patent Provisional Publication No. H11-204774) is illustrated in FIGS. 1A to 1H.

First, in the step shown in FIG. 1A, a buffer 11 is reserved in a water bath 10 made of Teflon (registered trade name), and native ferritin 21 including an inorganic particle 20 therein is dispersed in this buffer.

Next, in the step shown in FIG. 1B, a PBLH membrane 30 is overlaid on the liquid surface of the solution. Then, the pH is adjusted with an appropriate acid alkaline solution. Because the PBLH membrane surface is positively charged, the native ferritin 21 which is negatively charged is attached on the PBLH membrane.

Next, in the step shown in FIG. 1C, a base material (silicon substrate) 40 which had been subjected to a hydrophobic surface treatment is floated on the liquid surface on which the PBLH membrane 30 was overlaid, thereby allowing the PBLH membrane 30 on which the native ferritin 21 is attached to be adhered on the base material.

Next, in the step shown in FIG. 1D, the silicon substrate 40 having the adhered PBLH membrane 30 on which the native ferritin 21 is attached is removed from the water bath.

Next, in the step shown in FIG. 1E, after covering the surface on which the native ferritin 21 is attached with a buffer solution 11, ultraviolet irradiation is performed using a mask pattern 50. The native ferritin in the region on which ultraviolet ray was irradiated is decomposed, and dispersed in the solution.

Next, in the step shown in FIG. 1F, the silicon substrate 40 after executing the patterning shown in FIG. 1E is washed with water.

Next, in the step shown in FIG. 1G, the silicon substrate 40 is dried to obtain the pattern arrangement of the native ferritin including the inorganic particle therein.

Thereafter, in the step shown in FIG. 1H, a heat treatment at 500° C. is carried out in an inert gas 60 (for example, in nitrogen) to bake the native ferritin 21 including the inorganic particle therein and the PBLH membrane 30, thereby providing secondary pattern arrangement of the inorganic particles on the base material surface. This structure is further processed to give a structure required for the device as described above.

However, the SAM membrane is formed on the base material side, and patterning is executed on the SAM membrane using ultraviolet ray, or an LB membrane that is an adsorption membrane of the inorganic particle is utilized as the intermediate layer with respect to the a base material in the aforementioned conventional method. Therefore, there are possibilities that the steps may be complicated, or that impurities included in the constituents of the SAM membrane or the LB membrane, or in the solution remain on the arranged surface of the inorganic particles whereby causing adverse influences on the device.

Accordingly, an object of the present invention is to provide a technique for selectively and regularly arranging inorganic particles, in particular, those having a diameter of several to several ten nanometers in a necessary region and in a necessary amount with high mass productivity at low costs by allowing the inorganic particle to have a base material recognizing ability.

SUMMARY OF THE INVENTION

In order to accomplish the object described above, the first aspect of the present invention is characterized in that binding force between ferritin and the inorganic material on the substrate is controlled by a nonionic surface active agent. The nonionic surface active agent fundamentally has a function to attenuate the binding force between a protein and the base material on the substrate that is an inorganic substance through acting on the interface between them. Thus, this action enables control of the binding force between ferritin and the base material.

In other words, this procedure enables control of the proportion of the ferritin adsorbed on the part where arrangement is required and on the part where arrangement is not required (selectivity), and control of the amount of adsorption of the ferritin on the part where arrangement is required. This term "control" means rendering the ferritin itself to have an ability of augmenting inherent binding force between the substrate and the ferritin, or of lowering the force to the contrary (self-recognizing ability).

This self-recognizing ability makes it possible to arrange the ferritin in a specified inorganic material part on the substrate where arrangement of the inorganic particles is required, and to arrange the inorganic particles included in the ferritin.

On the other hand, when the inorganic particle is not included in ferritin, the inorganic particles are not arranged in the inorganic material part on the substrate, thereby enabling protection of the specified part with the ferritin.

The structure of conventional ferritin (native or recombinant ferritin (basket-shaped protein)) is illustrated in FIG. 2. Ferritin is a spherical particle having a diameter of about 12 nm and having a cavity (diameter: about 7 nm) inside thereof formed through binding of 24 subunits. Various inorganic material particles (core) can be incorporated in this cavity. One subunit has a specific tertiary structure as shown in the center of FIG. 2, which was analyzed in detail with X-ray analyses and the like revealing that it includes a combination of secondary structures of the α-helix and β-sheet.

Amino acid side chains are protruded from the skeleton (folded polypeptide main chain) of this protein in various directions, and the sequence of the amino acid residues allows each protein to have unique chemical characteristics. The ferritin surface reflects the features of the protruded amino acid residues, thereby determining the chemical characteristics of the entire protein (interaction with the base material, interaction among the proteins and the like).

The second aspect of the present invention is characterized in that the chemical characteristic of ferritin is altered by modifying this ferritin at the N-terminal part with a peptide (N-terminal modification peptide) thereby allowing the peptide to protrude from the ferritin surface. Furthermore, binding force between the ferritin and the inorganic base material is controlled by the modification with this N-terminal modification peptide.

The term "modification of N-terminal part of ferritin with a peptide" referred to herein involves both of: addition of an N-terminal modification peptide at the N-terminus of ferritin, and insertion of an N-terminal modification peptide subsequent to the N-terminal amino acid residue of ferritin (methionine residue).

Moreover, the third aspect of the present invention is characterized in that the peptide for modifying the N-terminus of the ferritin (N-terminal modification peptide) has one or more polar charged amino group(s). Examples of the polar charged amino group include lysine (K), arginine (R), histidine (H), aspartic acid (D) and glutamic acid (E). FIG. 3 illustrates the structure of the arginine (R) residue as the polar charged amino group. The peptide which modifies the N-terminal part has a flexible main chain with a structure that may be variable. Because of the structure having this flexible main chain protruded from the surface of the ferritin (FIG. 3, middle figure and right figure), the charged amino group shall be a factor of action to control the adsorbing force through recognizing the charge localized on the inorganic material surface.

Specifically, the present invention relates to a method for selectively arranging ferritin, the method comprising a first arrangement step in which a solution containing first ferritin and a nonionic surface active agent is added dropwise to a substrate having on the surface thereof a first part comprising a first inorganic material and a second part comprising a second inorganic material that is different from the first inorganic material, thereby arranging the first ferritin selectively in the first part, the first part comprising titanium or silicon nitride, and the second part comprising platinum or silicon oxide.

Although ferritin is nonselectively adsorbed to the inorganic material of the substrate, the present inventor first found that it is selectively adsorbed to a certain inorganic material by allowing a nonionic surface active agent to coexist.

It is preferred that the first part and the second part comprise any one combination selected from three combinations composed of: titanium and platinum, titanium and silicon oxide, and silicon nitride and silicon oxide, respectively.

It is more preferred that the first part and the second part comprise a combination of titanium and platinum, respectively.

It is more preferred that the first part and the second part comprise a combination of titanium and silicon oxide, respectively.

It is more preferred that the first part and the second part comprise a combination of silicon nitride and silicon oxide, respectively.

It is preferred that the concentration of the nonionic surface active agent is 0.01 v/v % or greater and 10 v/v % or less.

It is preferred that the subunit N-terminal part of the first ferritin is modified with a peptide set out in SEQ ID NO: 4.

The first ferritin may include an inorganic particle therein.

It is preferred that the second arrangement step in which a solution containing second ferritin but not containing any nonionic surface active agent is added dropwise to the substrate, thereby arranging the second ferritin in the second part is further included following the first arrangement step.

In this instance, the second ferritin may include an inorganic particle therein. Also, the first ferritin may not include an inorganic particle therein.

Using the method for arranging ferritin, a device can be produced by selectively arranging ferritin or the inorganic particles in the first part or the second part on the substrate.

According to the method for arranging ferritin of the present invention, when ferritin and the inorganic particle included therein are arranged and fixed on the base material surface, the physical adsorbing force between the ferritin and the inorganic material part formed on the base material surface can be controlled by adding a nonionic surface active agent, and secondary regular arrangement of the ferritin on the substrate is also enabled. According to the method for arranging ferritin of the present invention, the inorganic particles can be arranged in the region where required in a necessary amount, or the inorganic particles can be arranged on the substrate with high accuracy in a regular manner, with high mass productivity and favorable cost performances.

BRIEF DESCRIPTION OF THE DRAWINGS

FIG. 7A shows a scanning transmission electron micrograph of the substrate surface according to Comparative Example 2; and FIG. 7B shows a scanning transmission electron micrograph of the substrate surface according to Example 1.

FIG. 8A shows a scanning transmission electron micrograph of the substrate surface according to Example 2; and FIG. 8B shows a scanning transmission electron micrograph of the substrate surface according to Example 3.

FIG. 9A shows a scanning transmission electron micrograph of the substrate surface according to Example 3; and FIG. 9B shows a scanning transmission electron micrograph of the substrate surface according to Example 3 when Tween 80 in an amount of 0.5 v/v % was added.

FIG. 10A shows a schematic explanatory view with respect to Example 7; and FIG. 10B shows a scanning transmission electron micrograph of the substrate surface according to Example 7.

DETAILED DESCRIPTION OF THE INVENTION

The foregoing objects, other objects, features and advantages of the present invention will be apparent from the following detailed description of preferred embodiments with reference to attached drawings.

Modes for carrying out the present invention will be explained below with appropriate reference to the drawings. However, the present invention is not limited thereto.

PRINCIPLES OF THE PRESENT INVENTION

Principles of the present invention will be first explained. In this section, a method for arranging ferritin and the inorganic particle included in the ferritin on a substrate will be explained.

[Method for Arranging Ferritin]

Figure 4:
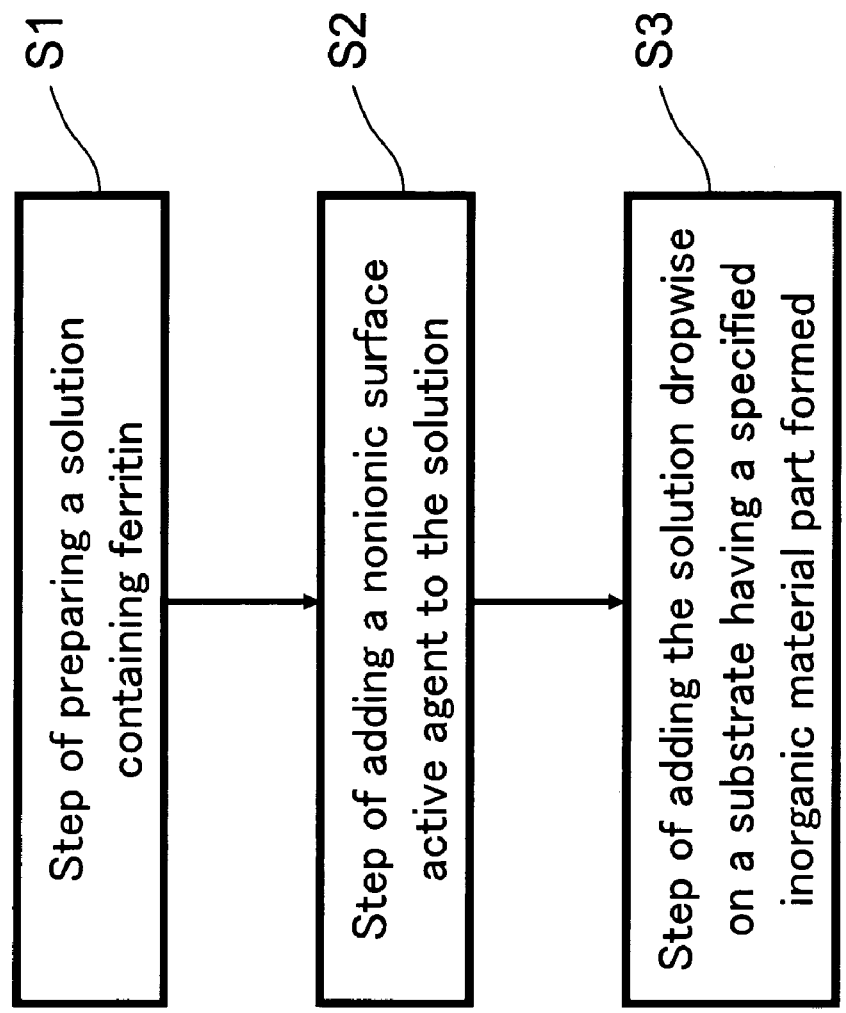
FIG. 4 shows an explanatory view illustrating the principles of the method for arranging ferritin of the present invention.

FIG. 4 shows a flow chart conceptually illustrating the method for arranging ferritin of the present invention.

As shown in FIG. 4, the method for arranging ferritin of the present invention includes three steps, i.e., steps S1 to S3.

First, in the step S1, a solution containing ferritin is prepared.

Next, in the step S2, a nonionic surface active agent is added to the solution prepared in the step S1.

Next, in the step S3, the solution prepared in the step S2 is added dropwise on the substrate having two or more inorganic material parts formed on the surface thereof. Accordingly, binding force between the ferritin and the inorganic material part on the substrate is altered by the addition of the nonionic surface active agent. Consequently, selective arrangement of the ferritin is enabled in either one of the inorganic material parts.

As the ferritin which may be used in the step S1, peptide-modified ferritin and conventional recombinant ferritin were used in the Embodiments of the present invention described later.

The step S1 and the step S2 are explained herein as each independent step, however, the step S1 and the step S2 can be also carried out at the same time as single step. Hereinafter, the method for manufacturing such ferritin will be explained.

<Method for Manufacturing Recombinant Ferritin>

First, a method for manufacturing recombinant ferritin will be explained without modification of the N-terminus with a peptide.

Although native ferritin (derived from equine spleen) is constructed by assembly of 24 subunits, there are L type and H type subunits having slightly different structures. Therefore, the native ferritin does not have a constant structure. In the following embodiment, recombinant ferritin constructed with only L type subunits was used.

First, a DNA encoding L type ferritin (SEQ ID NO: 1, 528 base pairs) was amplified with a PCR method to prepare a large amount of the L type ferritin DNA. Next, this L type ferritin DNA was cleaved at sites where restriction enzymes EcoRI and Hind III will specifically cleave (restriction enzyme sites). By this cleavage treatment, a solution of L type ferritin DNA fragments having restriction enzyme sites of EcoRI and Hind III was prepared. DNA electrophoresis of this solution was performed, and the DNA fragments encoding the L type ferritin alone were recovered and purified.

Figure 5:
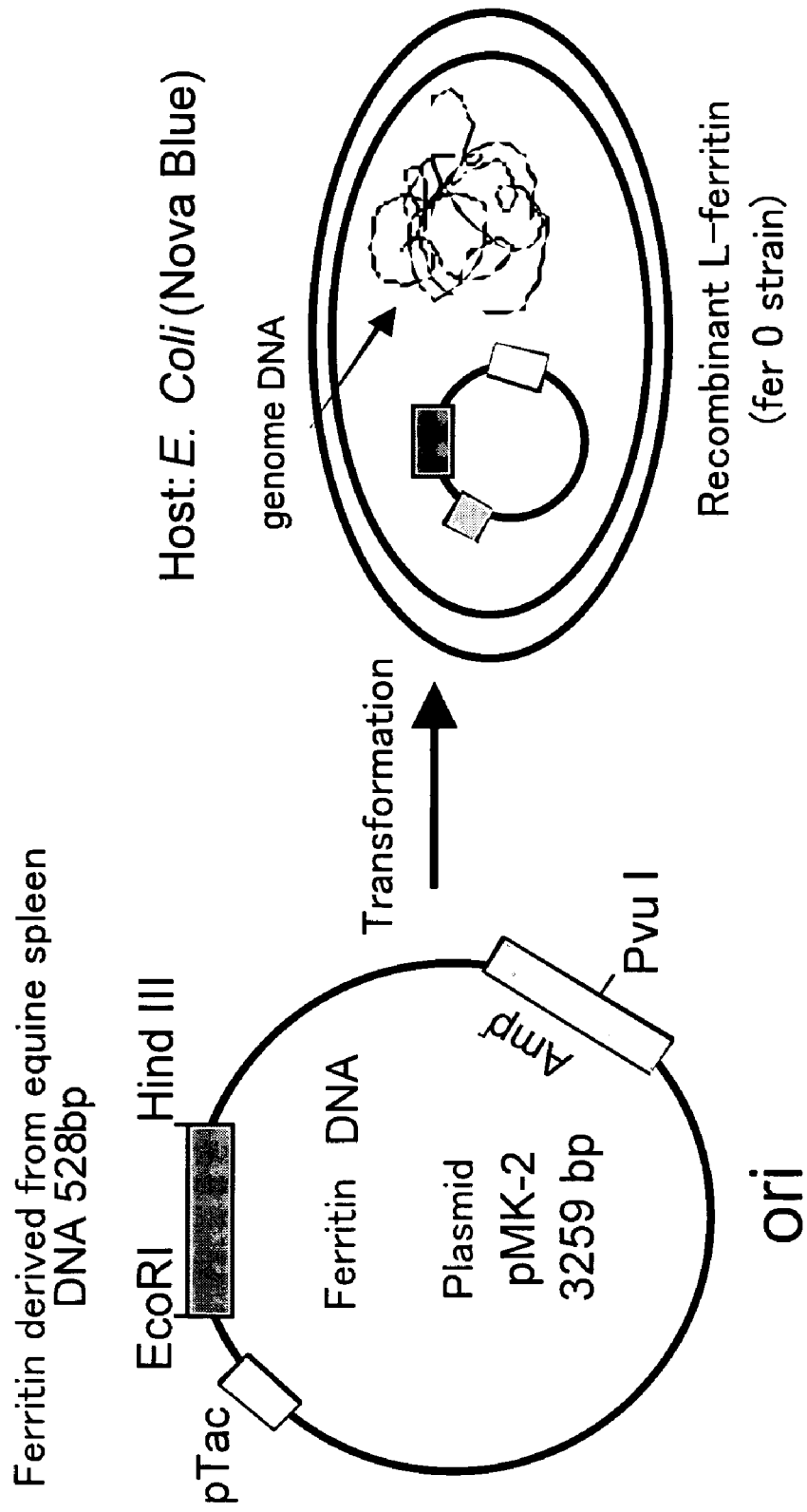
FIG. 5 shows a schematic view illustrating the principal construction of a plasmid of L type ferritin subunit, and incorporation of the plasmid into *Escherichia coli*.

Thereafter, this L type ferritin DNA fragment and a vector plasmid (pMK-2) treated with restriction enzymes EcoRI-Hind III were incubated to perfect ligation. Accordingly, a vector plasmid pMK-2-fer-0 having the L type ferritin DNA incorporated at the multicloning site (MSC) of the pMK-2 plasmid was produced. The vector plasmid pMK-2 employed was selected in light of advantages in obtaining a large amount of ferritin because it has Tac promoter as its promoter, and thus is characterized by the large copy number as a multicopy plasmid. Thus produced plasmid (pMK-2-fer-0) was introduced (transformed) into *E. coli* Nova Blue (Novagen), a strain of *Escherichia coli*, as a host, thereby yielding a recombinant L type ferritin strain (fer-0). Schematic view illustrating the principal construction of the plasmid of the L type ferritin subunit, and incorporation of the plasmid into *Escherichia coli* is shown in FIG. 5.

Then, in the method for arranging inorganic particles on the substrate described later, inclusion of inorganic particles required for a device were executed into thus produced recombinant ferritin. It was suggested that thermostability of the recombinant ferritin (fer-0) produced according to the aforementioned method is improved by the addition of the peptide to the amino terminus. Although the native ferritin had an allowable temperature limit of approximately 55° C., in contrast, fer-0 had an allowable temperature limit of 95° C. By virtue of this heat resistance, synthesis of nanoparticles utilizing a basket-shaped protein at a high temperature which had been conventionally impossible was enabled.

<Method for Manufacturing Ferritin Modified with Peptide>

Next, a method for manufacturing ferritin including a peptide having the amino acid sequence set out in SEQ ID NO: 4 inserted subsequent to the N-terminal residue (SEQ ID NO: 2) will be explained.

Figure 1A:
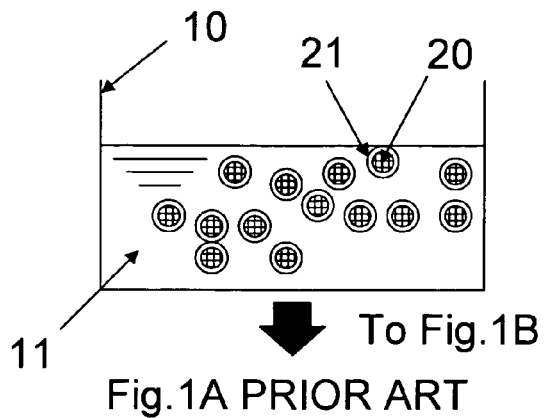
FIGS. 1A to 1H show an explanatory view illustrating the steps of a conventional method for arranging inorganic particles.
Figure 1B:
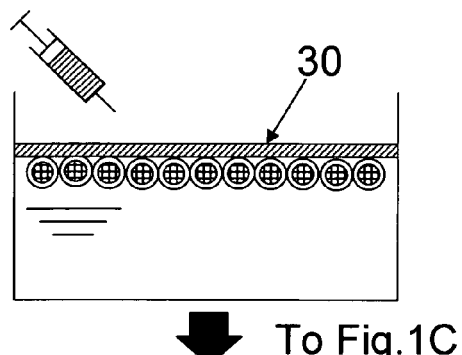
Figure 1C:
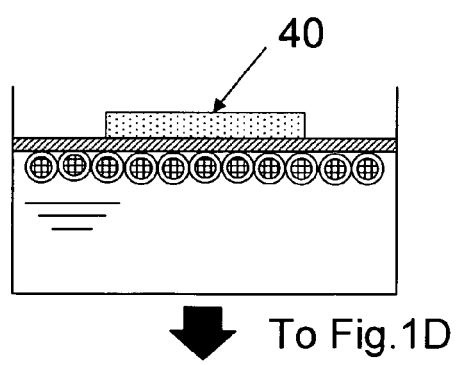
Figure 1D:
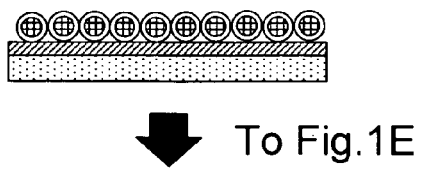
Figure 1E:
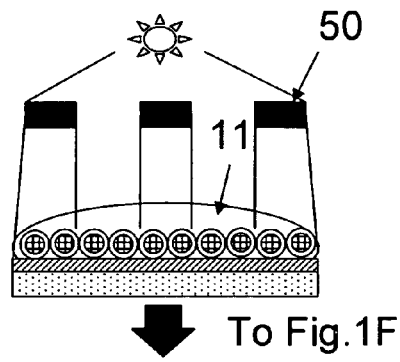
Figure 1F:
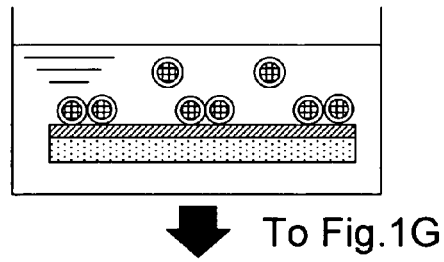
Figure 1G:
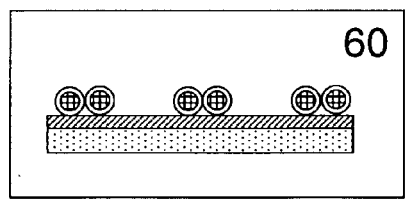
Figure 1H:
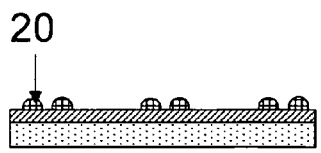
Figure 2:
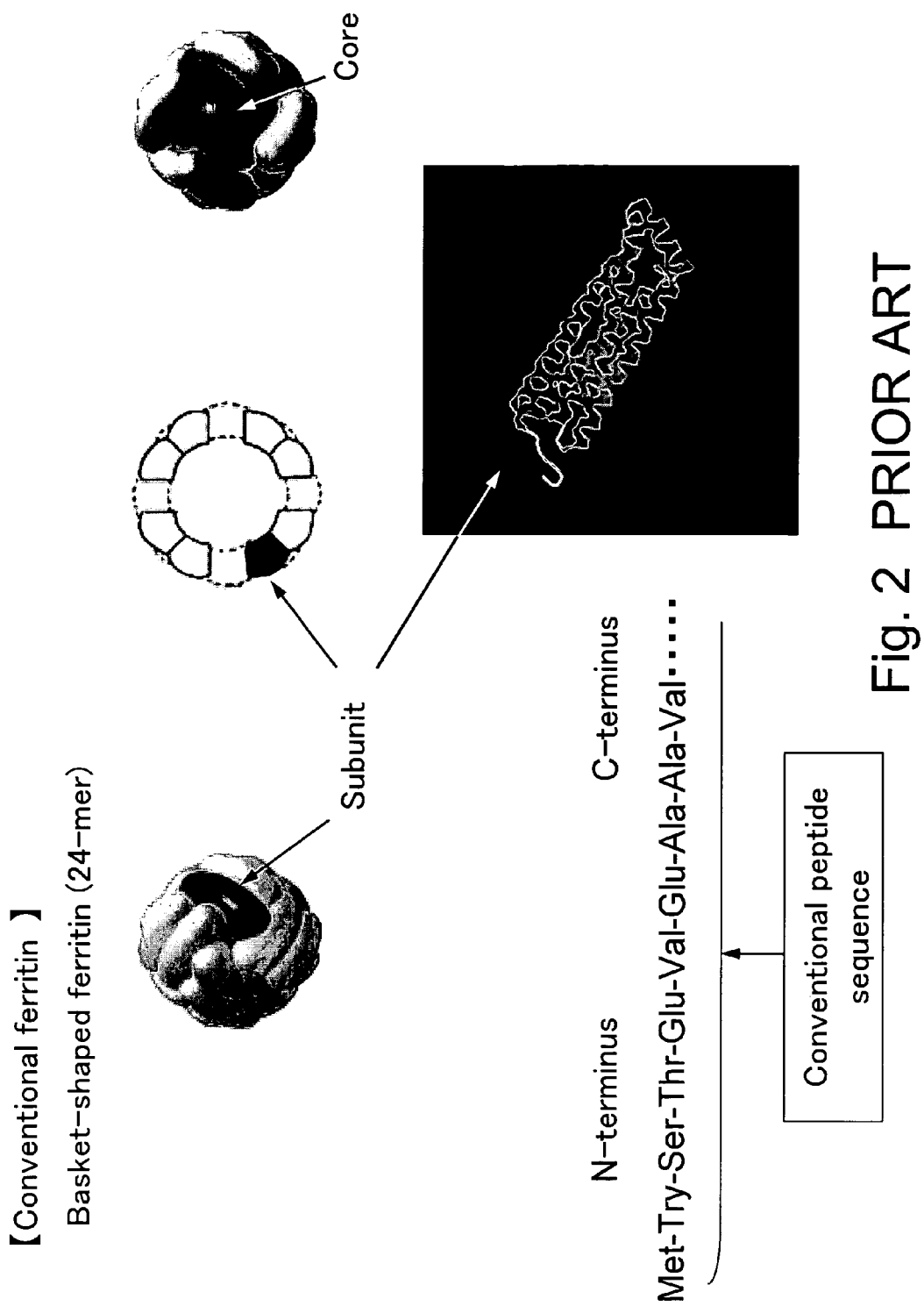
FIG. 2 shows an explanatory view illustrating the structure and the like of conventional ferritin.
Figure 3:
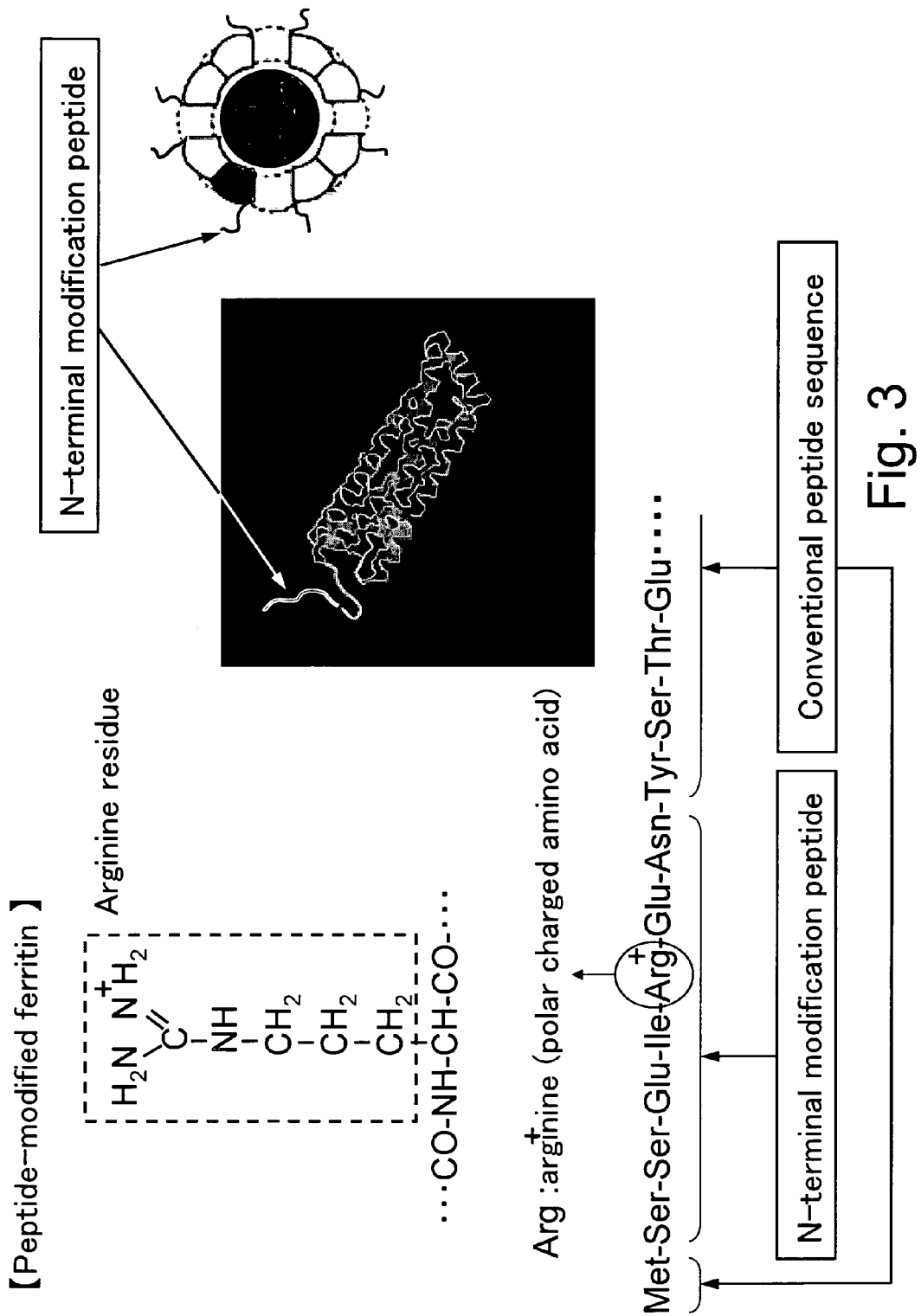
FIG. 3 shows an explanatory view illustrating the structure and the like of ferritin modified at the N-terminus with a peptide.

When the amino terminus (N-terminus) of the subunit constructing ferritin is modified with a peptide, a structure including the peptide protruded outside of the ferritin particle as shown in FIG. 3 is provided. Hence, modification of the surface of the ferritin fine particle with a peptide is enabled by addition or insertion of an arbitrary peptide at this N-terminal part.

Hereinafter, a specific method for manufacturing ferritin having the amino acid sequence set out in SEQ ID NO: 2 will be demonstrated. A full length gene of the L type subunit of native ferritin (derived from equine spleen) is set out in SEQ ID NO: 1. It was reported that 7 residues among amino residues synthesized from N-terminal 24 bases are processed and deleted in nature. In other words, ferritin having the amino acid sequence set out in SEQ ID NO: 2 should be synthesized from the DNA set out in SEQ ID NO: 1, however, ferritin having the amino acid sequence set out in SEQ ID NO: 3 is yielded in fact because 7 amino acid residues of from the second to the eighth are deleted from the N-terminus.

Accordingly, the chemical characteristic of the ferritin was altered by synthesizing without deletion of the N-terminal 7 amino acid sequences (SEQ ID NO: 4) to allow a flexible peptide with variable structure to be protruded outside of the ferritin particle, and thus, a method for controlling the adsorption of this ferritin modified with a peptide to the inorganic material in the presence of a nonionic surface active agent was found.

A base sequence (DNA) encoding peptide-modified ferritin having the peptide sequence set out in SEQ ID NO: 4 inserted subsequent to the N-terminal methionine residue of the subunit was designed, which was used in a PCR method to prepare a large amount of the DNA similarly to the aforementioned method for manufacturing recombinant ferritin. This DNA fragment required for the synthesis was introduced into a vector plasmid. Thus produced vector plasmid was introduced into *Escherichia coli* followed by proliferation (transformation) to perfect the synthesis of recombinant ferritin modified with a peptide (peptide-modified ferritin).

In the present invention, type of the peptide for modifying the N-terminal part of recombinant ferritin is not particularly limited, but recombinant ferritin including a peptide having the amino acid sequence set out in SEQ ID NO: 4 as the N-terminal modification peptide, inserted subsequent to the N-terminal methionine residue, i.e., recombinant ferritin having the amino acid sequence set out in SEQ ID NO: 2 was used in the Embodiments described below.

As explained in the foregoings, according to the method for arranging ferritin of the present invention, the steps are extremely simplified because binding force between ferritin and the specified inorganic material part of the substrate surface can be controlled by merely adding a nonionic surface active agent.

[Method for Arranging Inorganic Particles on the Substrate]

Next, the method for arranging inorganic particles of the present invention will be explained by way of FIGS. 6A and 6B. Herein, an example in which ferric oxide ($Fe_2O_3$) was used as the inorganic particle will be demonstrated.

Figure 6:
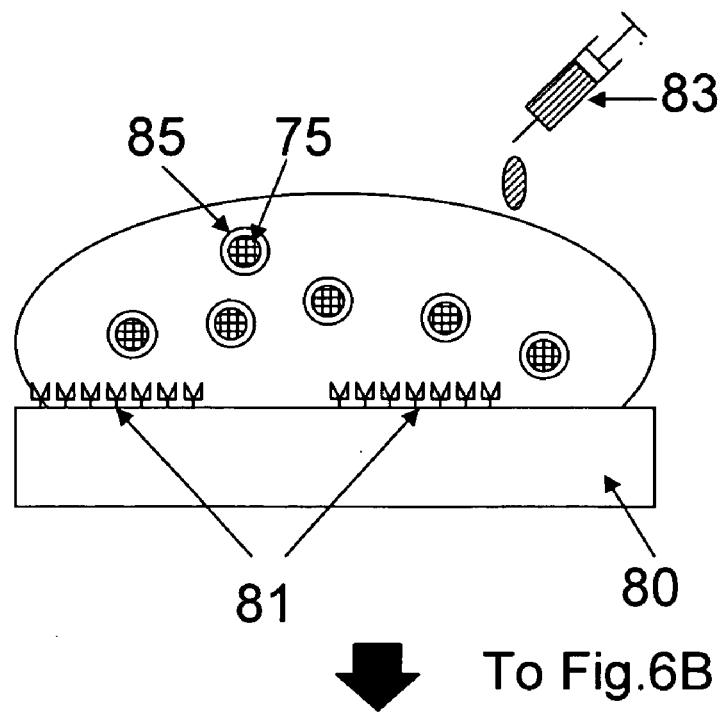
FIGS. 6A and 6B show an explanatory view illustrating the principles of the method for arranging inorganic particles of the present invention.
Figure 6:
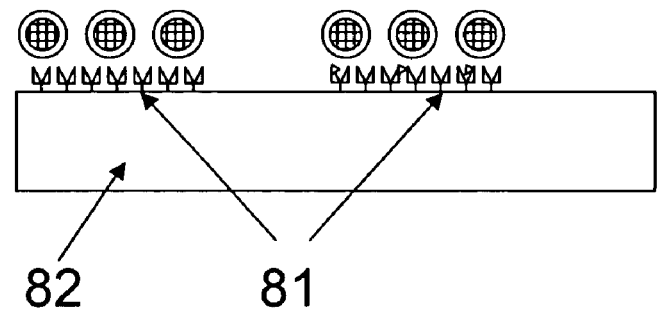

In the step shown in FIG. 6A, after adding dropwise a solution of conventional ferritin 85 including $Fe_2O_3$ 75 therein to which a nonionic surface active agent 83 was added onto a substrate 80 having a region 81 where arrangement of inorganic particles is required, followed by incubation for a given time period, the substrate was washed with pure water.

Next, in the step shown in FIG. 6B, because the conventional ferritin is adsorbed in the specified region 81 on the substrate 80, $Fe_2O_3$ 75 included therein can be arranged also in the specified region 81. As a consequence, the substrate 82 can be produced having the fine particles of $Fe_2O_3$ 75 selectively arranged only in the specified region.

Also, as the alternative example of the method described above, when the peptide-modified ferritin is used in place of the conventional ferritin, the amount of adsorption of the inorganic particles to the certain region 81 is markedly increased, and adsorption onto the substrate 80 with low interaction can be suppressed. Accordingly, further highly selective arrangement is enabled.

In Embodiments described below, the ferritin which had been including $Fe_2O_3$ therein was baked by subjecting the substrate to a heat treatment at 500° C. in nitrogen gas after washing with water, whereby allowing $Fe_2O_3$ to be fixed in the specified region 81. In place of nitrogen gas, inert gas or oxygen gas, hydrogen gas or the like can be also used.

Next, introduction of the inorganic particle into ferritin will be explained.

<Introduction of Inorganic Particle into Ferritin>

In the present invention, type of the inorganic particle to be included into the recombinant ferritin is not particularly limited, but in the foregoing descriptions and Embodiments described later, ferric oxide ($Fe_2O_3$) was used as the inorganic particle. Introduction of the $Fe_2O_3$ core into the peptide-modified ferritin was conducted as described below.

As the reaction solution, 0.5 mg/ml peptide-modified ferritin/100 mM HEPES-NaOH (pH 7.0) was prepared, and thereto was added 5 mM ammonium iron acetate. The reaction was allowed at 25° C. overnight, and the peptide-modified ferritin having the core of $Fe_2O_3$ formed was recovered from the solution following the reaction through molecular purification by centrifugal separation and gel filtration. The centrifugal separation was conducted under the conditions of 1,600 G for 10 min, and 10,000 G. for 30 min. Thus, unwanted portions other than the ferritin were eliminated stepwise as the precipitate, and then the peptide-modified ferritin having a $Fe_2O_3$ core formed therein was recovered from the finally remaining supernatant by ultracentrifugal separation at 230, 000 G for 1 hour as the pellet. Thus resulting peptide-modified ferritin was loaded on gel filtration using HPLC [column: TSK-GEL G4000SWXL PEEK/flow rate: 1 ml/min/buffer: 50 mM Tris-HCl (pH 8.0)+150 mM NaCl] to fractionate to give a peak of 24-mer (about 480 kDa). Solution of the fractionated peptide-modified ferritin was concentrated using an ultrafilter to obtain the peptide-modified ferritin including $Fe_2O_3$ therein.

In addition, by carrying out a similar operation to that described above on recombinant ferritin without modification of the N-terminus with a peptide, recombinant ferritin including $Fe_2O_3$ therein was obtained. Also, by carrying out a similar operation to that described above on the native ferritin (derived from equine spleen), native ferritin including $Fe_2O_3$ therein was obtained.

Hereinafter, specific embodiments of the present invention will be explained sequentially.

EMBODIMENT 1

Embodiment 1 of the present invention demonstrates a method for arranging ferritin and inorganic particles on a substrate. In this Embodiment, a Pt part and a Ti part are formed on a substrate as two kinds of inorganic material parts.

Specific examples of this Embodiment will be demonstrated by way of Examples below, and the effect thereof will be explained with reference to Comparative Examples. In the following Comparative Examples 1 and 2, and Reference Example, the nonionic surface active agent was not used.

COMPARATIVE EXAMPLE 1

In Comparative Example 1, inorganic particles were arranged on a substrate as described below.

First, native ferritin (manufactured by Sigma Corporation, derived from equine spleen) including $Fe_2O_3$ therein was adjusted to give the concentration of 2 mg/ml using a buffer solution (10 mM Tris-HCl, pH 8.0). On a Ti substrate having a platinum membrane (Pt membrane) formed on a part of its surface was added the native ferritin solution dropwise. After leaving to stand at room temperature for 1 hour, the substrate was washed with pure water. After washing, the substrate was subjected to a heat treatment according to the method described above, thereby allowing $Fe_2O_3$ to be fixed on the substrate.

Thereafter, a scanning transmission electron micrograph of the substrate surface was taken, and the number of $Fe_2O_3$ arranged on the Ti substrate and the Pt membrane was counted in a square of 200 nm. The number on the Ti substrate was 79, while the number on the Pt membrane was 76, exhibiting the selective arrangement ratio of 1.0.

Herein, the selective arrangement ratio means the ratio of the number of $Fe_2O_3$ adsorbed on the Ti substrate, $N_{(Ti)}$, to the number of $Fe_2O_3$ adsorbed on the Pt membrane, $N_{(Pt)}$, i.e., $N_{(Ti)}/N_{(Pt)}$.

COMPARATIVE EXAMPLE 2

In Comparative Example 2, a similar operation to that in Comparative Example 1 was carried out on the recombinant ferritin including $Fe_2O_3$ therein.

FIG. 7A shows a scanning transmission electron micrograph of the substrate surface in an experiment in which the recombinant ferritin including $Fe_2O_3$ therein was arranged on the Ti substrate including a Pt membrane formed on a part of its surface.

In FIG. 7A, when the number of $Fe_2O_3$ arranged on the Ti substrate and the Pt membrane was counted in a square of 200 nm, the number on the Ti substrate was 200, and in contrast, the number on the Pt membrane was 195, exhibiting the selective arrangement ratio of 1.0.

REFERENCE EXAMPLE

In Reference Example, a similar operation to that in Comparative Example 1 was carried out on the peptide-modified ferritin including $Fe_2O_3$ therein.

FIG. 7B shows a scanning transmission electron micrograph of the substrate surface in an experiment in which the peptide-modified ferritin including $Fe_2O_3$ therein was arranged on the Ti substrate including a Pt membrane formed on a part of its surface.

In FIG. 7B, the number of adsorption of $Fe_2O_3$ in a square of 200 nm was 116 on the Ti substrate, and was 100 on the Pt membrane, exhibiting the selective arrangement ratio of 1.2. Therefore, the selective arrangement ratio was increased by 20% when the peptide-modified ferritin was used, in comparison with the case in which the conventional ferritin was used. Accordingly, it was ascertained that ferritin became more apt to be adsorbed on the Ti substrate than on the Pt membrane.

Example 1

In Example 1, a similar operation to that in Reference Example was carried out using a solution to which 0.5 v/v % Tween 20 manufactured by ICI Inc., was added as a nonionic surface active agent, when native ferritin including $Fe_2O_3$ therein was prepared.

When the number of $Fe_2O_3$ arranged on the Ti substrate and the Pt membrane was counted in a square of 200 nm, the number on the Ti substrate was 79, while the number on the Pt membrane was 12, exhibiting the selective arrangement ratio of 6.6. Accordingly, addition of the nonionic surface active agent in an amount of 0.5 v/v % could allow the native ferritin to be selectively arranged on the Ti membrane.

Example 2

In Example 2, a similar operation to that in Reference Example was carried out using a solution to which 0.5 v/v % Tween 20 manufactured by ICI Inc., was added as a nonionic surface active agent, when recombinant ferritin including $Fe_2O_3$ therein was prepared.

FIG. 8A shows a scanning transmission electron micrograph of the substrate surface in an experiment in which the recombinant ferritin including $Fe_2O_3$ therein was arranged in the presence of the nonionic surface active agent, on the Ti substrate including a Pt membrane formed on a part of its surface.

Example 3

In Example 3, a similar operation to that in Reference Example was carried out using a solution to which 0.5 v/v % Tween 20 manufactured by ICI Inc., was added as a nonionic surface active agent, when peptide-modified ferritin including $Fe_2O_3$ therein was prepared.

FIG. 8B shows a scanning transmission electron micrograph of the substrate surface in an experiment in which the peptide-modified ferritin including $Fe_2O_3$ therein was arranged in the presence of the nonionic surface active agent, on the Ti substrate including a Pt membrane formed on a part of its surface.

Referring to FIGS. 8A and 8B, it is revealed that $Fe_2O_3$ was arranged on the Ti substrate and the Pt membrane with greater difference in the number of adsorption compared with FIGS. 7A and 7B. In FIG. 8A, the number of adsorption of $Fe_2O_3$ in a square of 200 nm was 150 on the Ti substrate, and in contrast, the number on the Pt membrane was 3, exhibiting the selective arrangement ratio of 50.0. Moreover, in FIG. 8B, the number of adsorption of $Fe_2O_3$ in a square of 200 nm was 146 on the Ti substrate, and was 1 on the Pt membrane, exhibiting the selective arrangement ratio of 146.0 which suggested remarkable improvement of the selectivity.

Hence, it was verified that addition of the nonionic surface active agent improved selective adsorptivity for the Ti substrate in any case in which the native ferritin, the recombinant ferritin or the peptide-modified ferritin is used. In particular, adsorbing force between ferritin and the inorganic base material could be controlled by modification of the ferritin surface with the peptide.

Additionally, because the selective arrangement ratio in Example 2 was 50.0, which was greater than the selective arrangement ratio of 6.6 in Example 1, it was indicated that the effect of improving selectivity for the inorganic base material (Ti substrate) by addition of the nonionic surface active agent was greater on the recombinant ferritin than on the native ferritin.

Example 4

In Example 4, a method of the arrangement was attempted in which a nonionic surface active agent was not added to the native ferritin solution but a solution containing the nonionic surface active agent was added dropwise to the substrate, followed by adding a native ferritin solution without including a nonionic surface active agent dropwise to the substrate. Accordingly, it was verified that the number of adsorption and selectivity that are almost equivalent to Example 1 in which the nonionic surface active agent was added to the native ferritin solution could be achieved.

Example 5

In Example 5, a method of the arrangement was attempted in which a nonionic surface active agent was not added to the recombinant ferritin solution but a solution containing the nonionic surface active agent was added dropwise to the substrate, followed by adding a recombinant ferritin solution without including a nonionic surface active agent dropwise to the substrate. Accordingly, it was verified that the number of adsorption and selectivity that are almost equivalent to Example 2 in which the nonionic surface active agent was added to the recombinant ferritin solution could be achieved.

Example 6

In Example 6, a method of the arrangement was also attempted in which a nonionic surface active agent was not added to the peptide-modified ferritin solution, but a solution containing the nonionic surface active agent was added dropwise to the substrate, followed by adding a peptide-modified ferritin solution without including a nonionic surface active agent dropwise to the substrate. Accordingly, it was verified that the number of adsorption and selectivity that are almost equivalent to Example 3 in which the nonionic surface active agent was added to the peptide-modified ferritin solution could be achieved.

Moreover, because the selective arrangement ratio in Example 5 was 50.0, which was greater than the selective arrangement ratio of 6.0 in Example 4, it was indicated that the effect of improving selectivity for the inorganic base material (Ti substrate) was greater on the recombinant ferritin than the native ferritin also in the case in which the substrate was treated with the nonionic surface active agent.

For reference, experimental results of Comparative Examples 1 to 2, Reference Example and Examples 1 to 6 are summarized in Table 1.

TABLE 1

| Method of arrangement | Native ferritin | | Recombinant ferritin | | Peptide-modified ferritin | |
|---|---|---|---|---|---|---|
| 1. No treatment of ferritin solution, substrate with surface activating agent | On Ti: 79 On Pt: 76 | Selective arrangement ratio: 1.0 [Comparative Example 1] | On Ti: 200 On Pt: 195 | Selective arrangement ratio: 1.0 [Comparative Example 2] | On Ti: 116 On Pt: 100 | Selective arrangement ratio: 1.2 [Reference Example] |
| 2. 0.5 v/v % nonionic surface activating agent added to ferritin solution | On Ti: 79 On Pt: 12 | Selective arrangement ratio: 6.6 [Example 1] | On Ti: 150 On Pt: 3 | Selective arrangement ratio: 50.0 [Example 2] | On Ti: 146 On Pt: 1 | Selective arrangement ratio: 146.0 [Example 3] |
| 3. Arranged by adding solution containing 0.5 v/v % surface activating agent dropwise. followed by addition of ferritin solution dropwise | On Ti: 77 On Pt: 13 | Selective arrangement ratio: 6.0 [Example 4] | On Ti: 150 On Pt: 3 | Selective arrangement ratio: 50.0 [Example 5] | On Ti: 140 On Pt: 1 | Selective arrangement ratio: 140.0 [Example 6] |

In addition, also in the cases in which 0.5 v/v % Tween 80 manufactured by ICI Inc., was added as the nonionic surface active agent, similar results to those in Table 1 were entirely achieved. Just for reference, scanning transmission electron micrographs of the substrate surface in the case in which 0.5 v/v % Tween 20 or Tween 80 was added in Example 3 are shown in FIGS. 9A and 9B, respectively.

As in the foregoings, the adsorbing force between the ferritin, and the Ti substrate and the Pt membrane of the substrate surface could be controlled by adding a nonionic surface active agent. In particular, use of the nonionic surface active agent in combination with the peptide-modified ferritin enabled synergistic control of the adsorption.

When the concentration of the added nonionic surface active agent was less than 0.006 v/v %, controllability of adsorption of the conventional ferritin and the peptide-modified ferritin was reduced, resulting in to decrease of the selective arrangement ratio. In contrast, when the concentration of the nonionic surface active agent was beyond 10 v/v %, the amount of adsorption to the Ti substrate was lowered. Therefore, judging from the practical usefulness, the nonionic surface active agent in the solution containing ferritin according to the present invention may be preferably in the range of the concentration of 0.006 v/v % or greater and 10 v/v % or less, and more preferably in the range of the concentration of 0.01 v/v % or greater and 1 v/v % or less.

Meanwhile, Tween 20 and Tween 80 used herein as the nonionic surface active agent are substances characterized by: belonging to polyoxyethylene sorbitans (polyoxyethylene sorbitan alkyl esters), being readily dissolved particularly at a low temperature, not having a group dissociable into an ion in the aqueous solution, and the hydrophilicity thereof being adjustable. General structural formulae of Tween 20 and Tween 80 are shown below.

TWEEN 20

[Chemical formula 1]

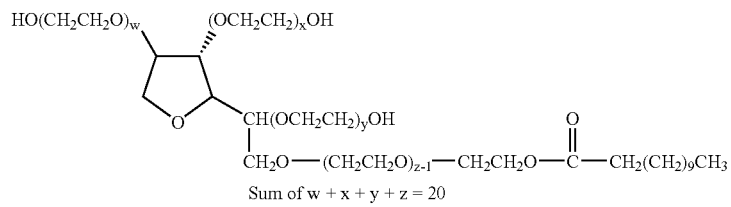

Sum of w + x + y + z = 20

TWEEN 80

[Chemical formula 2]

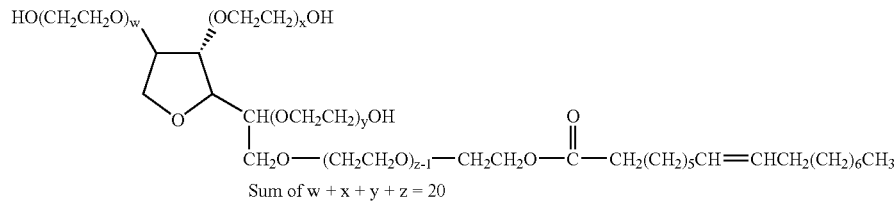

Sum of w + x + y + z = 20 subjected to a heat treatment according to the method described above, thereby allowing $Fe_2O_3$ 301 to be fixed on the substrate.

FIG. 10B shows a scanning transmission electron micrograph of the substrate surface after allowing the $Fe_2O_3$ 301 to be fixed as corresponded to FIG. 10A. $Fe_2O_3$ 301 was hardly arranged on the $SiO_2$ substrate 100, but was selectively arranged on the Ti membrane 200, therefore, it was verified that the peptide-modified ferritin 300 did not adsorb on the $SiO_2$ substrate 100 when it is coexistent with the nonionic surface active agent but specifically adsorbed on the Ti membrane 200.

EMBODIMENT 2

Embodiment 2 of the present invention demonstrates a method for arranging ferritin and inorganic particles on a substrate. In this Embodiment, two kinds of substrates, i.e., a substrate having a Ti membrane formed in a part on a $SiO_2$ substrate, and a substrate having a SiN membrane in a part on a $SiO_2$ substrate are used.

Specific examples of this Embodiment will be demonstrated by way of Examples below, and the effect thereof will be explained with reference to Comparative Examples.

Example 7

In connection with Example 7, FIG. 10A shows a schematic view illustrating results of an experiment in which peptide-modified ferritin 300 including $Fe_2O_3$ 301 therein was arranged on a silicon oxide ($SiO_2$) substrate 100 having a titanium membrane (Ti membrane) 200 formed in a part of the surface.

Peptide-modified ferritin 300 including $Fe_2O_3$ 301 therein was adjusted to give the concentration of 2 mg/ml with a buffer solution (10 mM Tris-HCl, pH 8.0), and thereto was further added 0.5 v/v % Tween 20 manufactured by ICI Inc., as a nonionic surface active agent. On the $SiO_2$ substrate 100 having a Ti membrane 200 formed in a part of the surface was added the peptide-modified ferritin solution dropwise. After leaving to stand at room temperature for 1 hour, the substrate was washed with pure water. After washing, the substrate was

COMPARATIVE EXAMPLE 3

In Comparative Example 3, the inorganic particles were arranged on the substrate through carrying out a similar operation to that in Example 5 except that Tween 20 was not added.

Figure 11B:
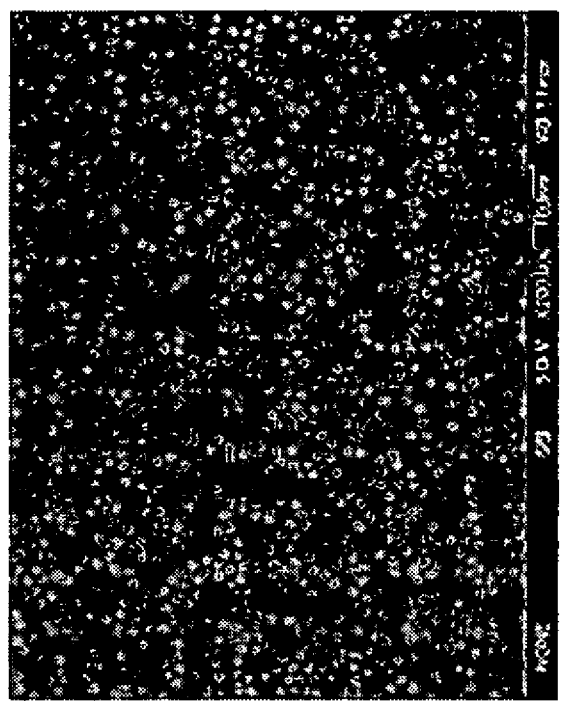
FIG. 11B shows a scanning transmission electron micrograph of the $SiO_2$ substrate surface according to Comparative Example 3.
Figure 11A:
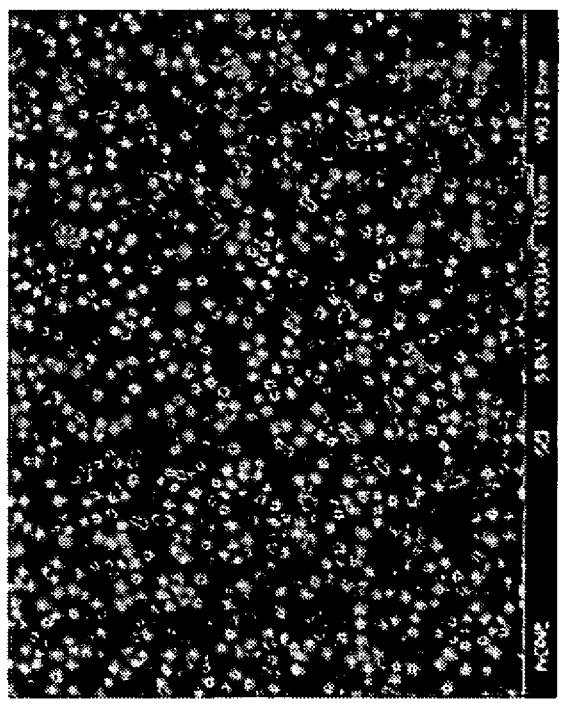
FIG. 11A shows a scanning transmission electron micrograph of the Ti membrane surface according to Comparative Example 3.

FIGS. 11A and 11B show scanning transmission electron micrographs of the substrate surface in Comparative Example 3. FIG. 11A shows the micrograph of the Ti membrane surface, while FIG. 11B shows the micrograph of the $SiO_2$ substrate surface. $Fe_2O_3$ was arranged on both the $SiO_2$ substrate surface and the Ti membrane surface at almost the same level. Hence, selectivity for the base material was not found at all. In other words, under the condition in which the nonionic surface active agent did not coexist, the peptide-modified ferritin did not exhibit selective adsorptivity for the Ti membrane and the $SiO_2$ substrate.

Accordingly, the adsorbing force between the peptide-modified ferritin, and the $SiO_2$ substrate and the Ti membrane of the substrate surface could be controlled by adding the nonionic surface active agent. Although Tween 20 was used as the nonionic surface active agent herein, the agent should not be limited thereto. For example, also in the cases in which Tween 80 manufactured by ICI Inc., was added at the same concentration, similar experimental results were achieved.

Example 8

In Example 8, an experiment in which the peptide-modified ferritin including $Fe_2O_3$ therein was arranged on a silicon oxide ($SiO_2$) substrate having a silicon nitride membrane (SiN membrane) formed in a part of the surface was conducted similarly to Example 7. The used buffer, nonionic surface active agent and the concentration thereof and the like are the same as in Example 7.

Figure 12B:
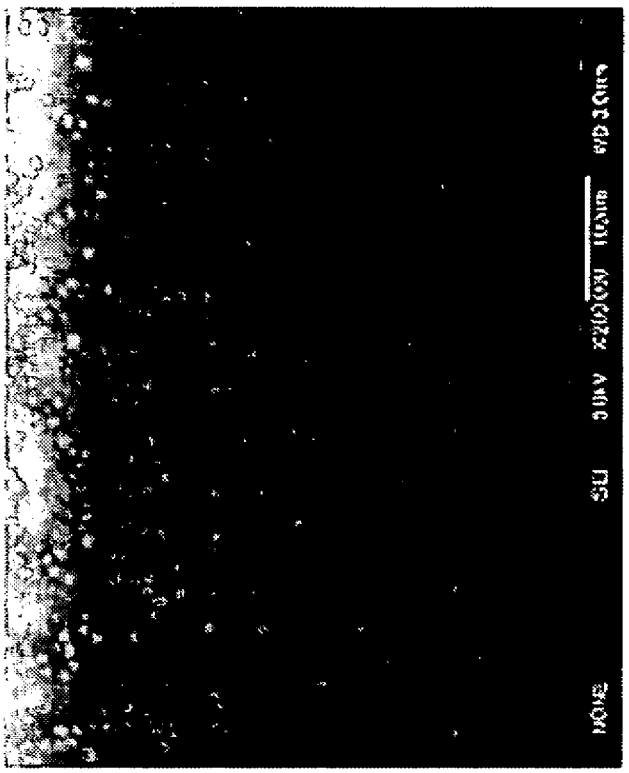
FIG. 12B shows a scanning transmission electron micrograph of the SiN membrane surface according to Example 8.
Figure 12A:
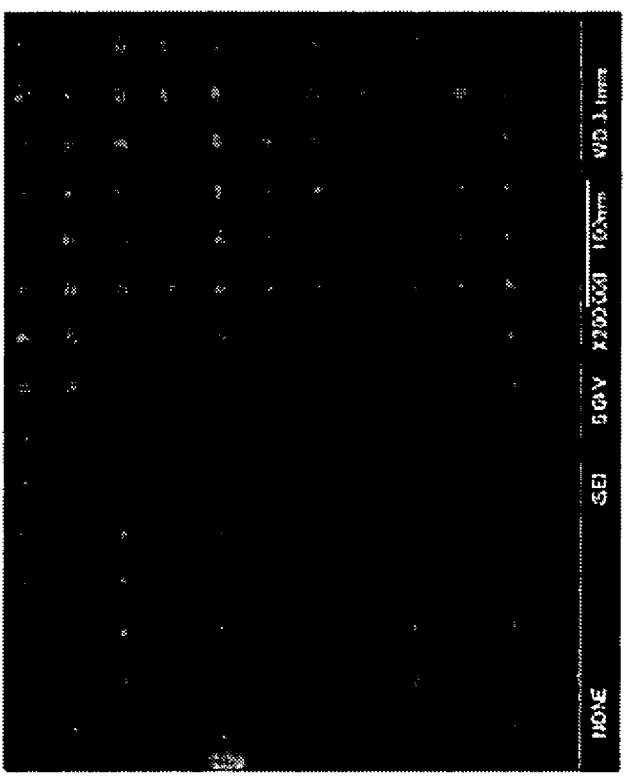
FIG. 12A shows a scanning transmission electron micrograph of the $SiO_2$ substrate surface according to Example 8.

FIGS. 12A and 12B show scanning transmission electron micrographs of the substrate surface in Example 8. FIG. 12A shows the micrograph of the $SiO_2$ substrate surface, while FIG. 12B shows the micrograph of the SiN membrane surface. Because $Fe_2O_3$ was not arranged on the $SiO_2$ substrate but was selectively arranged only on the SiN membrane, it was verified that the peptide-modified ferritin did not adsorb on the $SiO_2$ substrate in the presence of the nonionic surface active agent but specifically adsorbed on the SiN membrane.

COMPARATIVE EXAMPLE 4

In Comparative Example 4, the inorganic particles were arranged on the substrate through carrying out a similar operation to that in Example 8 except that Tween 20 was not added.

Figure 13B:
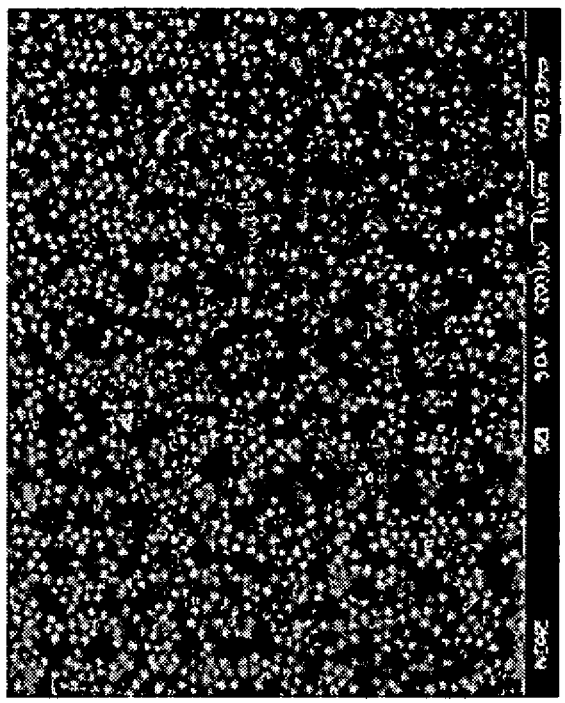
FIG. 13B shows a scanning transmission electron micrograph of the SiN membrane surface according to Comparative Example 4.
Figure 13A:
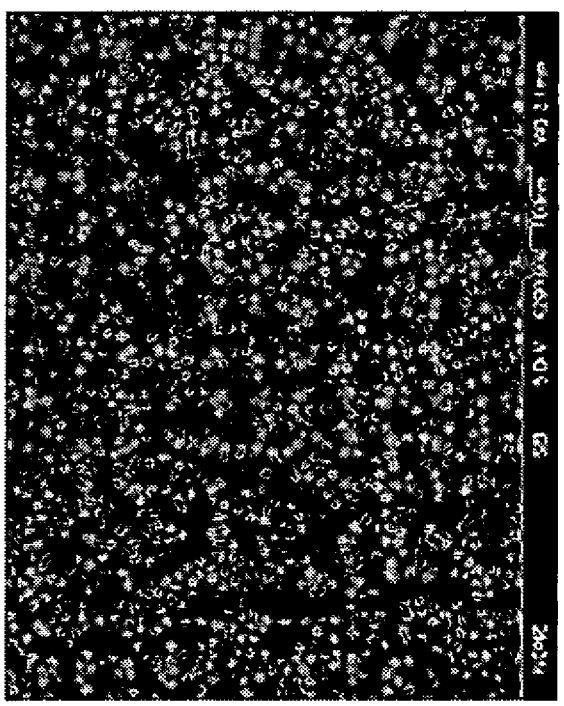
FIG. 13A shows a scanning transmission electron micrograph of the $SiO_2$ substrate surface according to Comparative Example 4.

FIGS. 13A and 13B show scanning transmission electron micrographs of the substrate surface in Comparative Example 4. FIG. 13A shows the micrograph of the $SiO_2$ substrate surface, while FIG. 13B shows the micrograph of the SiN membrane surface. $Fe_2O_3$ was arranged on both the $SiO_2$ substrate surface and the SiN membrane surface. Hence, selectivity for the base material was not found at all. In other words, under the condition in which the nonionic surface active agent was not present, the peptide-modified ferritin did not exhibit selective adsorptivity for the $SiO_2$ substrate and the SiN membrane. Accordingly, the adsorbing force between the peptide-modified ferritin, and the $SiO_2$ membrane and the SiN membrane of the substrate surface could be controlled by adding the nonionic surface active agent.

EMBODIMENT 3

Embodiment 3 of the present invention demonstrates a method for reverse-selective arrangement of ferritin and inorganic particles on a substrate.

<Method for Reverse-Selective Arrangement of Inorganic Particles Using Apoferritin>

In Embodiment 1 and 2, the method for arranging ferritin and inorganic particles in the region where ferritin is specifically adsorbed was explained. A method for arranging ferritin and inorganic particles in a region other than the region where the ferritin is specifically adsorbed in a reverse manner will be explained with reference to FIGS. 14A to 14E.

Figure 14A:
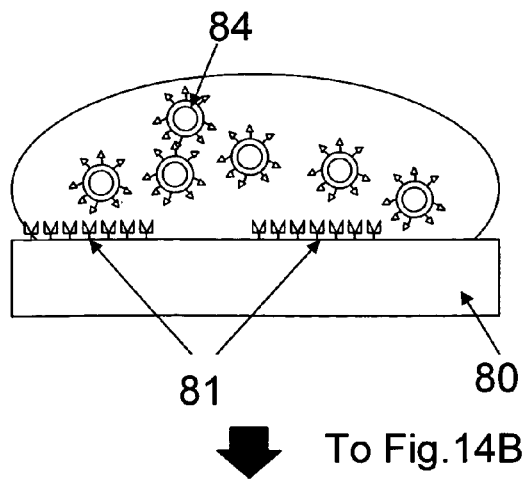
FIGS. 14A to 14E show an explanatory view illustrating the method for reverse-selectively arranging inorganic particles according to Embodiment 3 of the present invention.

First, in the step shown in FIG. 14A, a solution containing peptide-modified ferritin (apoferritin) 84 without including $Fe_2O_3$ therein and a nonionic surface active agent is added dropwise to a substrate 80 having a specified region 81 configured with a certain inorganic material in a part of the surface. Then, after incubation for a predetermined time period, the substrate is washed with pure water.

Figure 14B:
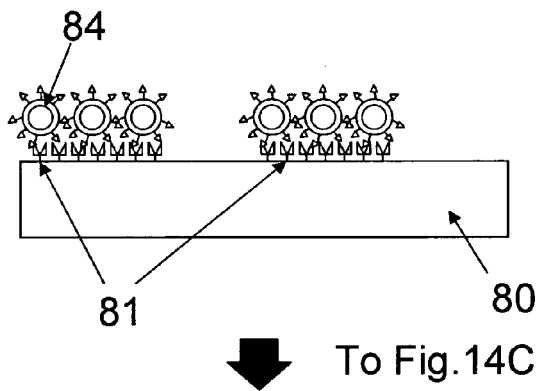

Next, in the step shown in FIG. 14B, the apoferritin 84 adsorbs only in the specified region 81, thereby giving the substrate 80 with selective arrangement.

Figure 14C:
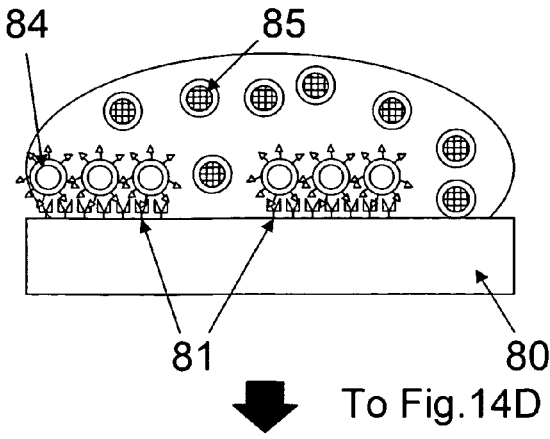

Next, in the step shown in FIG. 14C, a solution containing conventional ferritin including an inorganic particle therein 85 is added dropwise to the substrate 80, and a similar operation to that described above is carried out. In this step, any nonionic surface active agent is not used.

Figure 14D:
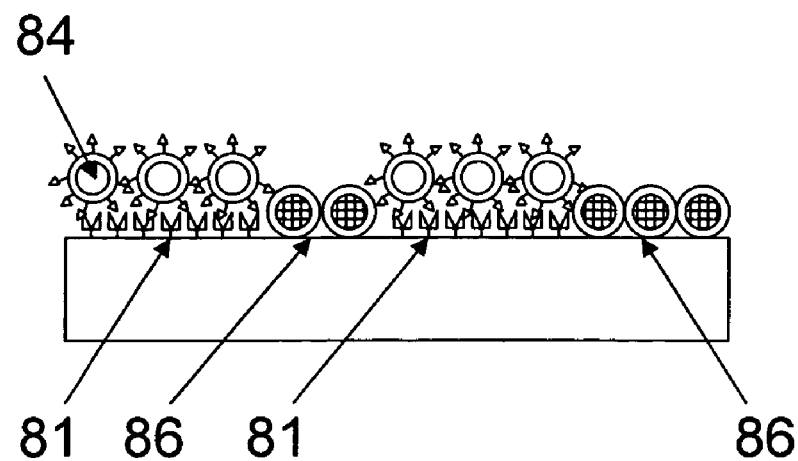

Next, in the step shown in FIG. 14D, the conventional ferritin 85 including an inorganic particle therein is adsorbed only in a region 86 where arrangement of the inorganic particles is required which is a region other than the specified region 81 where the apoferritin 84 was already adsorbed.

Figure 14E:
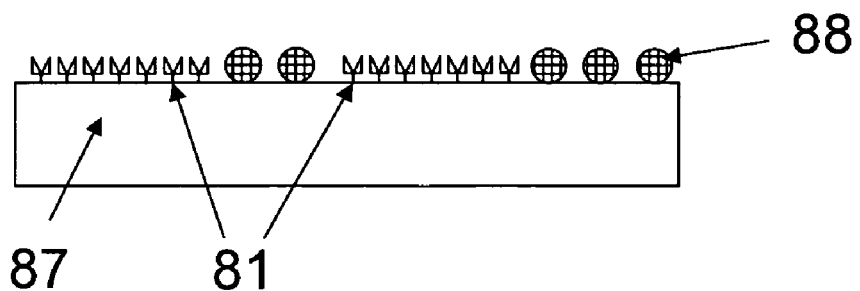

Thereafter, in the step shown in FIG. 14E, the substrate 80 is subjected to a heat treatment according to the method described above, whereby obtaining a substrate 87 having inorganic particle 88 reverse-selectively arranged in the region other than the specified region 81.

The protein including an inorganic particle therein is not limited to ferritin but other type of protein can be used. Also, in place of the ferritin including an inorganic particle therein, a protein without including an inorganic particle therein can be also reverse-selectively arranged. This technique shall be useful in the cases in which, for example, an enzyme having a certain function is arranged in a specified region on a substrate to manufacture a biosensor.

In addition, $Fe_2O_3$ is selectively arranged in a specified region on a substrate using the ferritin including $Fe_2O_3$ therein as an inorganic particle in the above Embodiments, however, just the same results shall be achieved when ferritin without including the inorganic particle therein is used.

From the foregoing description, many modifications and other embodiments of the present invention will be apparent to persons skilled in the art. Therefore, the foregoing description should be construed as merely illustrative exemplification, which was provided for the purpose of teaching the best embodiment for carrying out the present invention to persons skilled in the art. Details of the constitution and/or function of the present invention can be substantially altered without departing from the spirit thereof.

The present invention relates to a method for arranging ferritin or inorganic particles on a substrate surface with high mass productivity and favorable cost performances. In particular, a technique for selectively arranging inorganic particles having a diameter of several to several ten nm in a region where required, or for regularly arranging them in a nano-region. According to this technique, arrangement of fine particles of an inorganic material on a required base material in a self-selective manner on a nano-scale is enabled. The technique can be applied in manufacture steps in industrial fields of catalysts, sensors, biochips, transistors, semiconductor lasers, magnetic discs, displays and the like.

What is claimed is:

1. A method for selectively arranging ferritin and a substrate comprising:
   an arrangement step wherein a first solution containing ferritin and a nonionic surface active agent is exposed to a portion of said substrate consisting of a first inorganic material and a portion of said substrate consisting of a second inorganic material that is different from said first inorganic material, thereby arranging the ferritin selectively on said substrate portion consisting of the first inorganic material,
   wherein the ferritin is in direct-contact with said portion of substrate consisting of said first inorganic material,
   wherein said first inorganic material is titanium or silicon nitride, and
   said second inorganic material is platinum silicon oxide.

2. The method for selectively arranging ferritin according to claim 1 wherein said first inorganic material and said second inorganic material are both selected from the combinations consisting of: titanium and platinum, titanium and silicon oxide, and silicon nitride and silicon oxide.

3. The method for selectively arranging ferritin according to claim 2 wherein said first inorganic material is titanium and said second inorganic material is platinum.

4. The method for selectively arranging ferritin according to claim 2 wherein said first inorganic material is titanium and said second inorganic material is silicon oxide.

5. The method for selectively arranging ferritin according to claim 2 wherein said first inorganic material is silicon nitride and said second inorganic material is silicon oxide.

6. The method for selectively arranging ferritin according to claim 1 wherein the concentration of said nonionic surface active agent is between 0.01 v/v % and 10 v/v %.

7. The method for selectively arranging ferritin according to claim 1 wherein said ferritin in comprises SEQ ID NO: 4.

8. The method for selectively arranging ferritin according to claim 1 wherein said ferritin in said first solution includes an inorganic particle therein.

9. A method for selectively arranging ferritin on a substrate comprising:
   (a) an arrangement step wherein a first solution containing ferritin and a nonionic surface active agent is exposed to a portion of said substrate consisting of a first inorganic material and a portion of said substrate consisting of a second inorganic material that is different from said first inorganic material, thereby arranging the ferritin selectively on said substrate portion consisting of the first inorganic material,
   wherein the ferritin on said substrate portion consisting of said first inorganic material is in direct-contact with said portion of substrate consisting of said first inorganic material,
   wherein said first inorganic material is titanium or silicon nitride, and
   said second inorganic material is platinum or silicon oxide and, (b) wherein a second solution containing ferritin but not containing any nonionic surface active agent is exposed to said substrate, thereby selectively arranging ferritin on said portion of substrate consisting of said second inorganic material.

10. The method for selectively arranging ferritin according to claim 9 wherein said ferritin in said second solution includes an inorganic particle therein.

11. The method for selectively arranging ferritin according to claim 10 wherein said ferritin in said first solution does not include an inorganic particle therein.

\* \* \* \* \*

SEQUENCE LISTING

<160> NUMBER OF SEQ ID NOS: 4

<210> SEQ ID NO 1
<211> LENGTH: 528
<212> TYPE: DNA
<213> ORGANISM: Equus caballus -continued

<400> SEQUENCE: 1

```
atgagctccc agattcgtca gaattattct actgaagtgg aggccgccgt caaccgcctg    60
gtcaacctgt acctgcgggc ctcctacacc tacctctctc tgggcttcta tttcgaccgc   120
gacgatgtgg ctctggaggg cgtatgccac ttcttccgcg agttggcgga ggagaagcgc   180
gagggtgccg agcgtctctt gaagatgcaa aaccagcgcg gcggccgcgc tctcttccag   240
gacttgcaga agccgtccca ggatgaatgg ggtacaaccc cagacgccat gaaagccgcc   300
attgtcctgg agaagagcct gaaccaggcc ttttggatc tgcatgccct gggttctgcc    360
caggcagacc cccatctctg tagcttcttg tctagccact ccctagacga ggaggtgaaa   420
ctcatcaaga gatgggcgaa ccatctgacc aacatccaga ggctcgttgg ctcccaagct   480
gggctgggcg agtatctctt tgaaaggctc actctcaagc acgactaa                528
```

<210> SEQ ID NO 2
<211> LENGTH: 175
<212> TYPE: PRT
<213> ORGANISM: Artificial
<220> FEATURE:
<223> OTHER INFORMATION: Chemically Synthesized

<400> SEQUENCE: 2

```
Met Ser Ser Gln Ile Arg Gln Asn Tyr Ser Thr Glu Val Glu Ala Ala
1               5                   10                  15

Val Asn Arg Leu Val Asn Leu Tyr Leu Arg Ala Ser Tyr Thr Tyr Leu
            20                  25                  30

Ser Leu Gly Phe Tyr Phe Asp Arg Asp Asp Val Ala Leu Glu Gly Val
        35                  40                  45

Cys His Phe Phe Arg Glu Leu Ala Glu Glu Lys Arg Glu Gly Ala Glu
    50                  55                  60

Arg Leu Leu Lys Met Gln Asn Gln Arg Gly Gly Arg Ala Leu Phe Gln
65                  70                  75                  80

Asp Leu Gln Lys Pro Ser Gln Asp Glu Trp Gly Thr Thr Pro Asp Ala
                85                  90                  95

Met Lys Ala Ala Ile Val Leu Glu Lys Ser Leu Asn Gln Ala Leu Leu
            100                 105                 110

Asp Leu His Ala Leu Gly Ser Ala Gln Ala Asp Pro His Leu Cys Ser
        115                 120                 125

Phe Leu Ser Ser His Phe Leu Asp Glu Glu Val Lys Leu Ile Lys Lys
    130                 135                 140

Met Gly Asp His Leu Thr Asn Ile Gln Arg Leu Val Gly Ser Gln Ala
145                 150                 155                 160

Gly Leu Gly Glu Tyr Leu Phe Glu Arg Leu Thr Leu Lys His Asp
                165                 170                 175
```

<210> SEQ ID NO 3
<211> LENGTH: 168
<212> TYPE: PRT
<213> ORGANISM: Equus caballus

<400> SEQUENCE: 3

```
Met Tyr Ser Thr Glu Val Glu Ala Ala Val Asn Arg Leu Val Asn Leu
1               5                   10                  15

Tyr Leu Arg Ala Ser Tyr Thr Tyr Leu Ser Leu Gly Phe Tyr Phe Asp
            20                  25                  30

Arg Asp Asp Val Ala Leu Glu Gly Val Cys His Phe Phe Arg Glu Leu
        35                  40                  45
```

-continued

```
Ala Glu Glu Lys Arg Glu Gly Ala Glu Arg Leu Leu Lys Met Gln Asn
            50                  55                  60

Gln Arg Gly Gly Arg Ala Leu Phe Gln Asp Leu Gln Lys Pro Ser Gln
 65              70                  75                  80

Asp Glu Trp Gly Thr Thr Pro Asp Ala Met Lys Ala Ala Ile Val Leu
                85                  90                  95

Glu Lys Ser Leu Asn Gln Ala Leu Leu Asp Leu His Ala Leu Gly Ser
            100                 105                 110

Ala Gln Ala Asp Pro His Leu Cys Ser Phe Leu Ser Ser His Phe Leu
            115                 120                 125

Asp Glu Glu Val Lys Leu Ile Lys Lys Met Gly Asp His Leu Thr Asn
            130                 135                 140

Ile Gln Arg Leu Val Gly Ser Gln Ala Gly Leu Gly Glu Tyr Leu Phe
145                 150                 155                 160

Glu Arg Leu Thr Leu Lys His Asp
                165

<210> SEQ ID NO 4
<211> LENGTH: 7
<212> TYPE: PRT
<213> ORGANISM: Artificial
<220> FEATURE:
<223> OTHER INFORMATION: Chemically Synthesized

<400> SEQUENCE: 4

Ser Ser Gln Ile Arg Gln Asn
1               5
```